United States Patent [19]
Dahlquist et al.

[11] Patent Number: 5,094,535
[45] Date of Patent: Mar. 10, 1992

[54] SCANNING SENSOR SYSTEM INCLUDING AN FT-IR INTERFEROMETER

[75] Inventors: John A. Dahlquist, Palo Alto; Joseph F. Binkowski, Los Altos, both of Calif.

[73] Assignee: Measurex Corporation, Cupertino, Calif.

[21] Appl. No.: 417,961

[22] Filed: Oct. 6, 1989

[51] Int. Cl.⁵ .............................. G01B 9/02; G01J 3/45
[52] U.S. Cl. .................................................... 356/346
[58] Field of Search ......................................... 356/346

[56] References Cited

U.S. PATENT DOCUMENTS 4,871,142 10/1989 DeMey, II ......................... 248/632

*Primary Examiner*—Davis L. Willis
*Assistant Examiner*—Matthew W. Koren
*Attorney, Agent, or Firm*—Burns, Doane, Swecker & Mathis

[57] ABSTRACT

An on-line scanning sensor system includes first and second horizontally extending guide members connected by side members to define a rigid box-like frame, and a support structure for suspending the box-like frame via vibration-absorbing devices such that vibrations are substantially attenuated before reaching the guide members. Further, the system includes a carriage mounted on the first guide member for scanning motion across a traveling web of sheet of material, and interferometer components mounted to the carriage for splitting and recombining infrared light and for directing a collimated beam of the recombined light onto the traveling sheet. Still further, the system includes a detector for receiving light from the interferometer components during scanning.

10 Claims, 3 Drawing Sheets

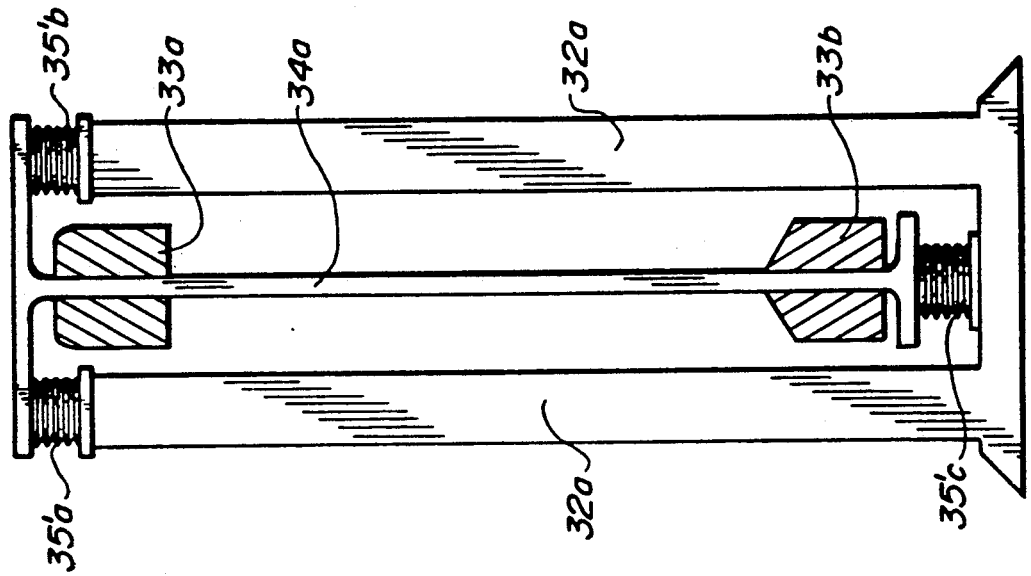
FIG._1A
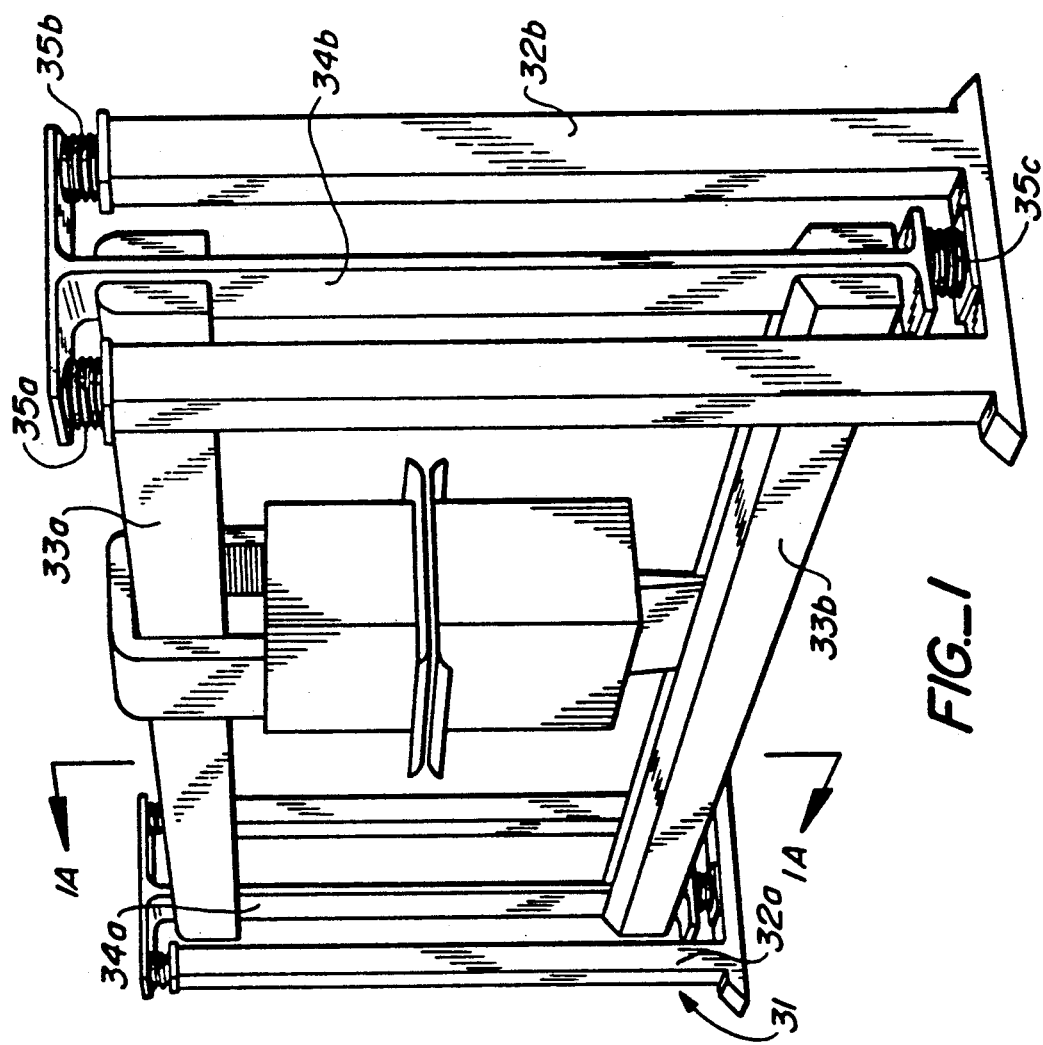
FIG._1

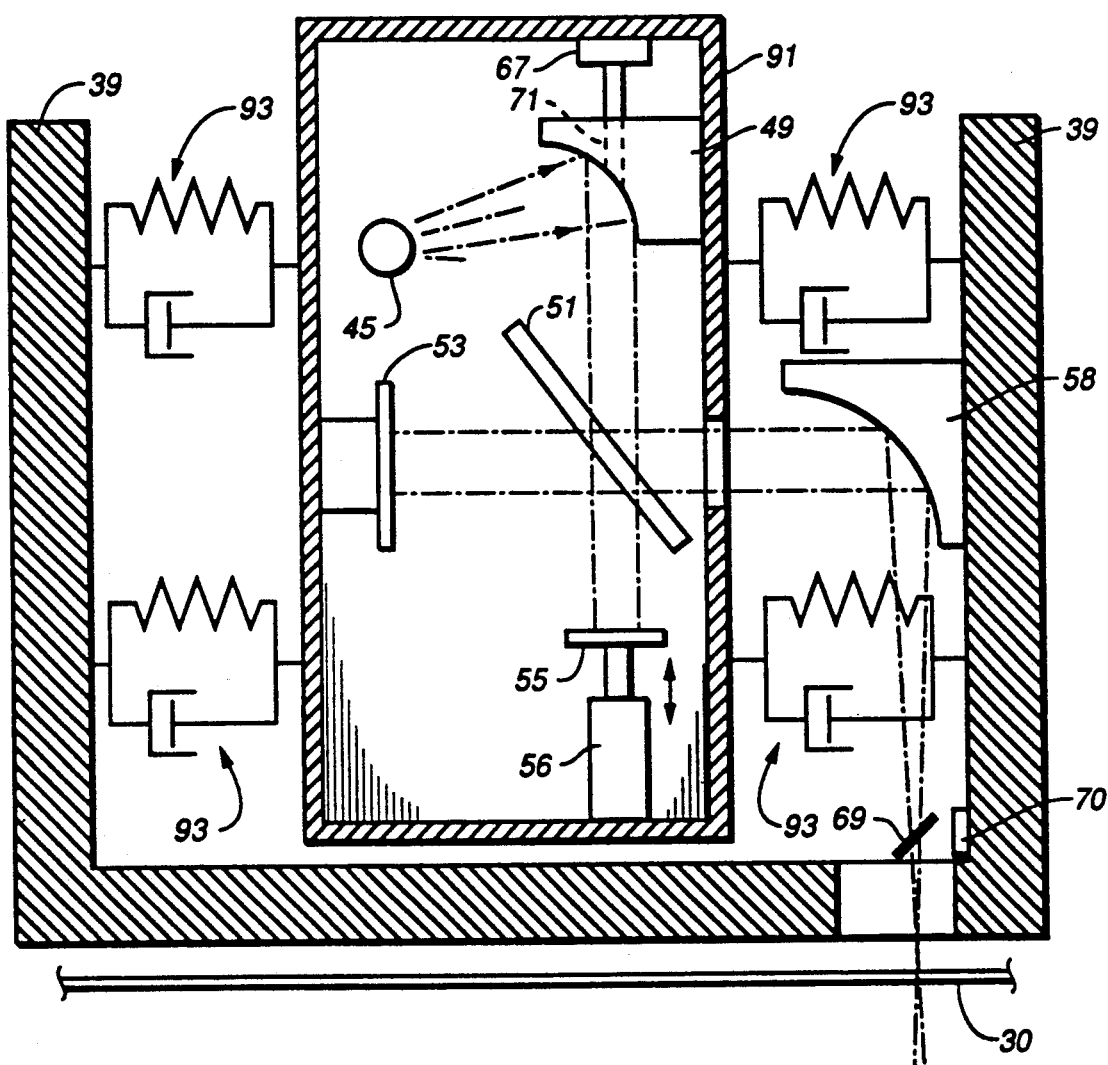
FIG._2
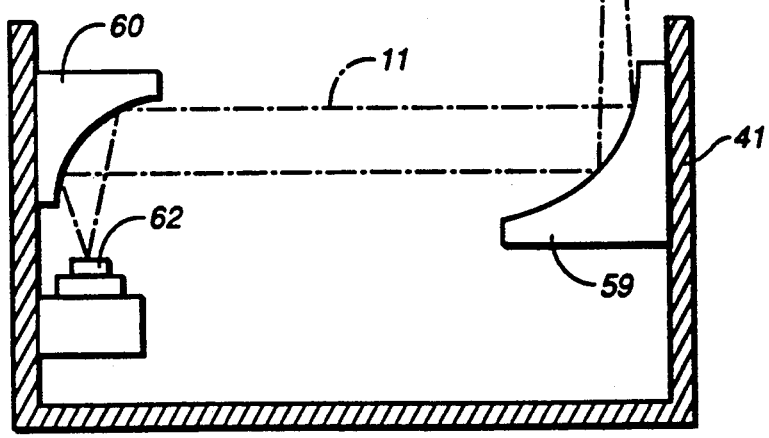

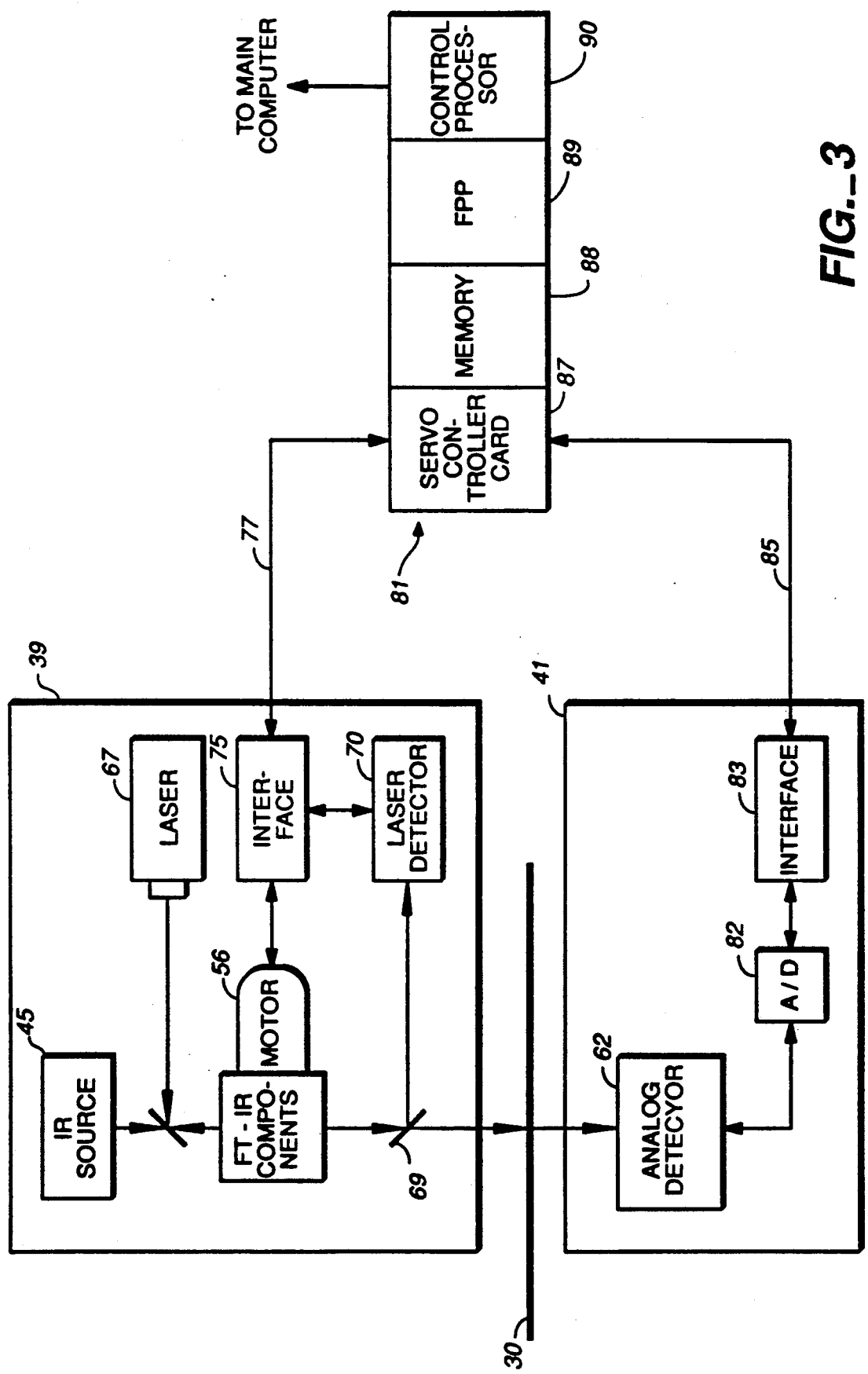
FIG._3

SCANNING SENSOR SYSTEM INCLUDING AN FT-IR INTERFEROMETER

BACKGROUND OF THE INVENTION

1. Field of the Invention

The present invention generally relates to the on-line detection of characteristics of sheet materials and, more particularly, to spectrometric methods for on-line detection of characteristics of sheet materials.

2. State of the Art

It is often desirable to obtain measurements of selected characteristics of sheet materials during manufacture. Although various properties of sheet materials can be detected by off-line laboratory testing, such tests often are not practical because of the time required for sample acquisition and analysis. Also, laboratory testing has the shortcoming that samples obtained for testing may not accurately represent sheet material that has been produced.

To overcome the drawbacks of laboratory testing of sheet materials, various sensor systems have been used for detecting sheet properties "on-line," i.e., on a sheet-making machine while it is operating. Typically, on-line sensor devices are operated to periodically traverse, or "scan," traveling webs of sheet material during manufacture. Scanning usually is done in the cross direction; i.e., in the direction perpendicular to the direction of sheet travel. Depending upon the sheet making operation, cross-directional distances can range up to about 400 inches or more. Typically, the rate of travel of a sheet through a scanning sensor system ranges from about forty to about four-hundred feet per minute.

Although a wide variety of scanning sensor devices have been used for on-line measurements of sheet materials, there have been difficulties in attempts to use on-line spectrometers based upon interferometers for such purposes. In part, the difficulties arise because interferometers normally are not designed for use in manufacturing environments where the instruments may be subjected to substantial vibrations from heavy and high-speed rotating machinery. Also, difficulties arise in using interferometers in on-line applications because on-line scanning sensors usually only view a sample area of a traveling sheet only for a limited time, whereas laboratory-type interferometers normally can analyze a fixed-position sample for as long as necessary to obtain a complete spectral display. Still other difficulties in applying conventional (e.g., laboratory) interferometers to on-line applications arise because the laboratory instruments are normally bulky.

SUMMARY OF THE INVENTION

Generally speaking, the present invention provides an on-line scanning sensor system including a mid-infrared spectrophotometric analyzer, such as an interferometer, that can be used on-line in manufacturing environments.

In the preferred embodiment according to the present invention, the system comprises the combination of:

first and second horizontally extending guide members connected by side members to define a rigid box-like frame;

a support structure for supporting the frame;

vibration-absorbing suspension system for suspending the frame from the support structure such that vibrations are substantially attenuated before reaching the guide members;

a carriage mounted on the first guide member for scanning motion across a traveling web of sheet of material;

interferometer components mounted to be carried by the first carriage and including devices for splitting and recombining infrared light and for directing a collimated beam of the recombined light onto the traveling web of sheet material; and a detector for receiving light from the interferometer component means as it travels during scanning.

In the preferred embodiment, the interferometer components include at least a source of infrared light, a beam splitter, a fixed planar mirror, a movable planar mirror, and a first parabolic mirror. Further in the preferred embodiment, the system includes a second carriage for scanning motion in registration with the first carriage, and the detector is carried by the second carriage for receiving light transmitted through the sheet material. Alternatively, the detector means can be carried by the first carriage means for receiving light that is reflected from the sheet material.

Still further in the preferred embodiment, the vibration-absorbing suspension system includes pneumatic spring mounts that support the frame structure such that vibrations exceeding about six hertz are substantially attenuated.

BRIEF DESCRIPTION OF THE DRAWINGS

The present invention can be further understood by reference to the following description and appended drawings which illustrate the preferred embodiments of the invention. For purposes of clarity, identical parts are given the same reference numbers in the various drawing figures. In the drawings:

FIG. 1 is a pictorial view of a scanning sensor system that employs a spectrometer based upon an interferometer in accordance with the present invention;

FIG. 1A is a cross-sectional view of the scanning system of FIG. 1;

FIG. 2 is a schematic diagram of an interferometer according to the present invention for use in the scanning sensor system of FIG. 1; and FIG. 3 is a functional block diagram of the interferometer of FIG. 2.

DETAILED DESCRIPTION OF THE PREFERRED EMBODIMENT

FIG. 1 generally shows an on-line scanning sensor system for analyzing traveling sheets of material. Except for the fact that the scanning sensor system includes a spectrometer based upon an interferometer, the external appearance of the system is generally similar to conventional scanning systems. Thus, the illustrated scanning sensor system includes a stationary frame, generally designated by the number 31, having a pair of upright end members 32a and 32b that stand on a factory floor for supporting a pair of parallel guide members 33a and 33b that extend horizontally across the opposite faces of a traveling sheet.

The frame of the scanning sensor system of FIG. 1 differs from conventional scanning sensor systems, however, in several respects. For example, the parallel guide members are rigidly connected by side members 34a and 34b to form a unitary box-like structure independent of the upright members 32a and 32b. In the preferred embodiment, the box-like structure is resiliently supported from the upright end members by resilient elements. In the illustrated embodiment, three resilient elements are mounted at the near end of the frame, and those elements are designated 35a, 35b and 35c, respectively. Three other resilient support elements 35'a, 35'b, and 35'c are similarly mounted at the far end of the frame.

As best shown in FIG. 1A, the resilient supports 35'a, 35'b and 35'c for the box-like structure comprised of the two guide members (33a and 33b) and the two side members (34a and 34b) are pneumatic spring mounts. Such mounts are commercially available under the trademark Stabl-Levl from Barry Controls Company of Waterton, Mass. In practice, it is preferred that the mounts have a resonant frequency of about three hertz so that they effectively attenuate vibrations above about six hertz.

The illustrated scanning sensor system also includes first and second carriage members 36 and 38 that are mounted to travel on the guide members 33 and 35, respectively. In practice, the carriage members are connected to a drive system (not shown) to be driven back and forth across sheet 30 at a rate of, for instance, about one foot per second.

As further shown in FIG. 1, the scanning sensor system includes first and second scanning heads 39 and 41 that are connected to travel with carriage members 36 and 38, respectively, back and forth along guide members 33 and 35 in registration with one another to scan across a sheet 30. As will be explained in greater detail below, first scanning head 39 contains the components of a Fourier Transform Infrared (FT-IR) interferometer except for detector components. As also will be further explained below, the detector components of the FT-IR interferometer are included in second scanning head 41.

FIG. 2 shows the interferometer components carried in first scanning head 39. Generally speaking, those components include a source of infrared light 45, a collimating mirror 49 for collimating light from source 45, a beam-splitting mirror 51, and first and second planar mirrors 53 and 55. First planar mirror 53, as is typical in interferometers, is fixed in position. In the illustrated embodiment, second planar mirror 55 is selectively driven by a motor 56 perpendicular to the incident beam.

FIG. 2 also shows the detector components carried in second scanning head 41. Generally speaking, those components include second and third parabolic mirror 59 and 60, and a photosensitive detector 62. It should be understood that all of the components in the second scanning head are fixed in position for travel with the head. Photosensitive detector 62 is a conventional device that provides analog output signals that are generally linearly related to the intensity of the incident light.

The operation of the components within scanning heads 39 and 41 of FIG. 2 will now be described. In operation, light source 45 directs divergent light, normally in the mid-infrared spectrum of wavelengths, onto collimating mirror 49. In turn, the collimating mirror directs collimated light onto beam-splitting mirror 51. The beam splitting mirror then splits the light so that it travels to fixed mirror 53 and movable 55 along two separate optical paths. Both mirrors 53 and 55 reflect light back to the beam-splitting mirror which, in turn, partially reflects and partially transmits the light to a parabolic mirror 58. Accordingly, as movable mirror 55 translates back and forth, the collimated light that reaches parabolic mirror 58 includes components that interfere both constructively and destructively.

In contrast to conventional interferometers, however, the components in scanning head 39 in FIG. 2 do not transmit light onto a stationary sample and then to a stationary detector. Instead, parabolic mirror 58 directs light onto the surface of the traveling web of sheet material 30. The light which passes through the sheet is collected by second parabolic mirror 59 carried by scanning head 41. From the second parabolic mirror, generally collimated light is directed to a third parabolic mirror 60 that, in turn, focuses the light onto photosensitive detector 62. Typically, the interferograms provided by the system each contain data from up to several square inches of the scanned sheet material.

As mentioned above, the scanning sensor system of FIGS. 1 and 2 is particularly designed to operate in environments that include vibrations that could, unless compensated for, adversely affect the measurements provided by the system. In other words, the scanning sensor system is designed to operate in factory floor environments. In such environments, vibrations can arise, for example, from sheetmaking machinery or from the components of the drive for the scanning sensor system. Such vibrations, unless compensated for, can adversely affect the accuracy of the sensor system by randomly increase or decrease the retardation distance within the interferometer.

FIG. 2 shows means for further reducing the effects of vibrations on the accuracy of the scanning sensor system. More particularly, in the illustrated embodiment, all of the components within housing 39 except for parabolic mirror 58 are mounted on a rigid frame 91 that is connected to housing 39 by vibration-absorbing suspension devices 93. The vibration-absorbing system is further described in co-pending U.S. patent application Ser. No. 07/417,919 filed Oct. 6, 1989 and in application Ser. No. 07/417,315 filed Oct. 5, 1989 now U.S. Pat. No. 5,030,007. Both of those applications are commonly assigned herewith and their disclosure is hereby incorporated by reference in its entirety.

As described in the co-pending patent application, rigid frame 91 in FIG. 2 is mounted such that the center of suspension provided by the vibration-absorbing suspension devices 93 coincides with the collective center of gravity of rigid frame 91 and the components mounted thereon. Such mounting allows the rigid frame to undergo translational motion (i.e., straight line motion) but prevents rotational movement in response to vibrations. More particularly, because the centers of suspension and gravity coincide, vibrations that cause translational motion of the rigid frame do not affect the angle at which light strikes parabolic mirror 58 and, hence, do not change its point of focus.

Further with regard to FIG. 2, it should be noted that the point of focus of parabolic mirror 58 is generally coincident with the surface of traveling sheet 30. In practice, precise coincidence is not required. In fact, where a sheet is transparent, the point of focus of parabolic mirror 58 preferably is spaced substantially from the sheet surface. In such cases, the beam diameter preferably is between about 0.3 and 0.6 inches when the beam strikes the sheet.

In addition to the above-discussed components, scanning head 39 of FIG. 2 includes a laser reference system. In the illustrated embodiment, the laser reference system comprises a laser source 67, a second beam-splitting mirror 69, and a laser detector 70. In the illustrated embodiment, laser source 67 is positioned to direct its light through an aperture 71 in parabolic mirror 49 such that, upon emergence from the parabolic mirror, the light follows the same path as the infrared light. Also in the illustrated embodiment, second beam-splitting mirror 69 is mounted to reflect light to laser detector 70 before the light passes through sheet 30.

The laser reference system of FIG. 2 can be used for several purposes. Preferably, laser detector 70 is AC coupled, which is to say that it detects only variations in signal magnitude. Thus, output signals from the laser detector provide single frequency interferograms. Points such as the maxima, minima, or zero-crossings of the interferograms can be used as reference points for accurately determining the relative position of movable mirror 55 within scanning head 39. Such points can also be used for determining when Fourier transforms are to be performed on output signals from infrared detector 62 in scanning head 41.

FIG. 3 shows, in functional form, the components of the scanning sensor system of the present invention. For instance, the diagram indicates that both infrared source 45 and laser source 67 direct light into scanning head 39. The diagram also indicates motor 56 that drives the movable mirror within scanning head 39. Still further, the diagram indicates that the beams of infrared and laser light are coaxial as they emerge from scanning sensor head 39 and that the laser light is reflected by beam splitting mirror 69 to detector 70.

As further shown in FIG. 3, both motor 56 and laser detector 70 interface with a circuit board 75 carried by scanning head 39. The circuit board provides control signals to the motor and receives signals from the laser detector. A communication link 77 connects circuit board 75 to a system control module 81 that will be described below in detail. Preferably, the communications link is a bi-directional RS 422 communications bus. The signals that pass through the bus include information signals from motor 56, motor control signals, and signals indicating zero-crossings of the laser interferograms.

As still further shown in FIG. 3, scanning head 41 includes photosensitive detector 62 as well as an analog-to-digital convertor 82 and an interface circuit board 83. A second communication link 85 connects circuit board 83 to system control module 81. Here again, it is preferred that the communications link is a bi-directional RS 422 communications bus. In practice, the signals on link 85 include digital signals from A/D convertor 82, and timing signals that control the timing of the output signals from A/D convertor 82. In practice, it is preferred that output signals from the convertor are provided simultaneously with zero-crossings of the output signals from laser detector 70 carried by scanning head 39.

In the embodiment shown in FIG. 3, system control module 81 comprises a servo controller card 87, a binary memory 88, a floating point processor (FPP) section 89, and a control processor 90. Signals from the control module are provided to a main computer at a remote location. In practice, signals from the control module indicate detected sheet properties at a rate of at least two measurements per second in real time.

In practice, the control processor 90 is a high-speed, 16-bit microprocessor-based computer which is dedicated to the scanning sensor system. Generally speaking, processor 90 operates to identify characteristic peaks and wave forms of the absorption spectra of the scanned sheet materials and to calculate individual component weights based upon absorption spectra. In turn, such measurements can be used for layer weight determination or thickness monitoring. The measurements can also be used for control in "real-time" to improve product consistency and quality.

For example, measurements provided by the scanning sensor system of FIGS. 1 through 3 can be used to provide on-line measurements of the characteristics of polymeric sheet materials such as, for example, polyethylene, polypropylene, ethylene vinyl alcohol, polyvinylidene chloride, Nylon, Surlyn, ethylene vinyl acetate, alone or in co-extruded combinations. In practice, the sheet materials can have single or multiple layers, each comprised of a different substance. The detected infrared absorbencies of the sheet materials can be used to calculate the weights and thicknesses of layers within scanned sheets The foregoing has described the principles, preferred embodiments and modes of operation of the present invention. However, the present invention should not be construed as being limited to the particular embodiments discussed For example, rather that using the two scanning heads 39 and 41, the detector components from scanning head 41 can be mounted in scanning head 39 for receiving and detecting light that is reflected from a traveling sheet as the interferometer components scans across the sheet. Accordingly, the above-described embodiments should be regarded only as illustrative, and it should be appreciated that workers skilled in the art may make variations in those embodiments without departing from the invention as defined by the following claims.

What is claimed is:

1. An on-line scanning sensor system for detecting characteristics of sheet materials by spectrometric methods comprising:
   a frame means having first and second horizontally extending guide members connected by side members to define a rigid box-like frame;
   support means for supporting the frame means;
   vibration-absorbing suspension means for suspending the frame means from the support means such that vibrations are substantially attenuated between the frame means and the support means;
   first carriage means mounted on the first guide member for scanning motion across a traveling sheet of material;
   interferometer component means mounted to be carried by the first carriage means, the interferometer component means including means for splitting and recombining infrared light and for directing a collimated beam of the recombined light onto a traveling web of sheet material; and
   detector means for receiving light from the interferometer component means as it travels during scanning across a traveling sheet.

2. A system according to claim 1 wherein the interferometer component means includes at least a source of infrared light, a beam splitting means, a fixed planar mirror means, a movable planar mirror means, and a first parabolic mirror means.

3. A system according to claim 2 wherein the vibration-absorbing suspension means comprise pneumatic spring mounts.

4. A system according to claim 2 wherein the vibration-absorbing suspension means substantially attenuate vibrations exceeding about six hertz.

5. A system according to claim 2 further including upright means for supporting the frame means, and the vibration-absorbing suspension means comprise pneumatic spring mounts that are mounted to the upright means for supporting the frame means.

6. A system according to claim 1 further including second carriage means for scanning motion across a traveling sheet of material in registration with the interferometer component means.

7. A system according to claim 6 wherein the detector means is carried by the second carriage means for receiving light from the interferometer component means as it travels during scanning across a traveling sheet.

8. A system according to claim 6 wherein second mirror means and the detector means are carried by the second carriage means for receiving light from the interferometer component means as it travels during scanning across a traveling sheet.

9. A system according to claim 8 wherein the vibration-absorbing suspension means substantially attenuate vibrations exceeding about six hertz.

10. A system according to claim 1 wherein the detector means is carried by the first carriage means for receiving light that is reflected from a traveling sheet as the interferometer component means scans across the sheet.

* * * * *